US008795422B2

(12) United States Patent
Ganapathiappan et al.

(10) Patent No.: US 8,795,422 B2
(45) Date of Patent: Aug. 5, 2014

(54) NAPHTHALOCYANINE DYE AND INK CONTAINING THE SAME

(75) Inventors: Sivapackia Ganapathiappan, Los Altos, CA (US); Jayprakash C. Bhatt, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 263 days.

(21) Appl. No.: 13/387,482

(22) PCT Filed: Aug. 31, 2009

(86) PCT No.: PCT/US2009/055504
§ 371 (c)(1),
(2), (4) Date: Jan. 27, 2012

(87) PCT Pub. No.: WO2011/025501
PCT Pub. Date: Mar. 3, 2011

(65) Prior Publication Data
US 2012/0139994 A1 Jun. 7, 2012

(51) Int. Cl.
*C09D 11/02* (2014.01)
*C09B 47/04* (2006.01)
*G01N 21/00* (2006.01)
*C09B 47/067* (2006.01)
*C07D 487/22* (2006.01)
*C09D 11/00* (2014.01)

(52) U.S. Cl.
CPC .......... *C07D 487/22* (2013.01); *C09B 47/0678* (2013.01); *C09B 47/0675* (2013.01); *C09D 11/328* (2013.01)
USPC ........ 106/31.49; 540/129; 540/130; 540/132; 250/338.5

(58) Field of Classification Search
USPC ....................... 106/31.49; 540/129, 130, 132; 250/338.5
See application file for complete search history.

(56) References Cited

U.S. PATENT DOCUMENTS

| 4,622,179 | A | 11/1986 | Eda |
| 5,709,717 | A | 1/1998 | Reddig et al. |
| 5,780,621 | A | 7/1998 | Harms et al. |
| 6,498,249 | B1 | 12/2002 | Snow et al. |
| 7,005,518 | B2 | 2/2006 | Peng et al. |
| 7,449,058 | B2 | 11/2008 | Patel |
| 7,559,983 | B2 | 7/2009 | Starling |
| 7,579,064 | B2 * | 8/2009 | Vonwiller et al. .......... 106/31.49 |
| 7,658,792 | B2 * | 2/2010 | Indusegaram et al. ..... 106/31.49 |
| 2003/0092907 | A1 | 5/2003 | Snow et al. |
| 2004/0171827 | A1 | 9/2004 | Peng et al. |
| 2004/0187734 | A1 | 9/2004 | Ozawa et al. |

(Continued)

FOREIGN PATENT DOCUMENTS

| EP | 0134518 | 3/1985 |
| WO | WO-2008046129 | 4/2008 |
| WO | WO 2010/019138 A1 * | 2/2010 |

OTHER PUBLICATIONS

European Examination Report for European Application No. 09848846.3 mailed Feb. 25, 2013.

(Continued)

*Primary Examiner* — Helene Klemanski

(57) ABSTRACT

The present disclosure includes naphthalocyanine dyes or fused naphthalocyanine dyes represented by one of the general structures I to XV; inkjet ink formulations including the naphthalocyanine dyes; and a detection system (300) including the dyes.

15 Claims, 2 Drawing Sheets

(56) References Cited

U.S. PATENT DOCUMENTS

| | | |
|---|---|---|
| 2005/0039274 A1 | 2/2005 | Yang et al. |
| 2005/0200803 A1 | 9/2005 | Snow et al. |
| 2006/0030704 A1 | 2/2006 | Vonwiller et al. |
| 2006/0162615 A1 | 7/2006 | Patel |
| 2006/0201387 A1 | 9/2006 | Patel |
| 2008/0006177 A1 | 1/2008 | Indusegaram |
| 2011/0135815 A1* | 6/2011 | Ganapathiappan et al. .. 427/160 |
| 2011/0204234 A1 | 8/2011 | Ganapathiappan et al. |
| 2012/0092428 A1* | 4/2012 | Ganapathiappan et al. .. 347/102 |
| 2012/0137928 A1 | 6/2012 | Ganapathiappan et al. |

OTHER PUBLICATIONS

European Search Report for European Application No. 09848846.3 mailed on Jan. 30, 2013.

International Search Report for PCT/US2009/055504 mailed on Apr. 30, 2010.

Written Opinion for PCT/US2009/055504 mailed on Apr. 30, 2010.

* cited by examiner

NAPHTHALOCYANINE DYE AND INK CONTAINING THE SAME

BACKGROUND

Phthalocyanine and naphthalocyanine are macrocylic compounds that have strong pigmenting power attributed to their alternating nitrogen and carbon atom central ring structures of porphyrin compounds (i.e., benzene-porphyrin and naphthalene-porphyrin compounds, respectively). As such, phthalocyanine and naphthalocyanine are useful in dyes with a plethora of applications in biology and chemistry as well as industry. The central nitrogen atoms of a pyrroline portion of the porphyrin compounds may be either complexed with a metal or are metal-free to provide further variations in color. For example, metal-free phthalocyanine has a blue-green color while copper-complexed phthalocyanine has a blue color (Pigment Blue 15). Other substitutions on the phthalocyanine and naphthalocyanine compounds invoke other colors as well. In general, these dyes exhibit absorption at wavelengths up to 1000 nm. Phthalocyanine and naphthalocyanine are chemically stable compounds that are normally not soluble in water or aqueous solutions. Water soluble groups can be added to increase the water solubility of the phthalocyanine and naphthalocyanine compounds. To solubilize either of their structures, one or both of highly ionic groups and soluble ethylene oxide groups can be attached to dissolve them in water. Unfortunately, commercial water soluble cyanine, phthalocyanine and naphthalocyanine compounds with near IR absorption have relatively poor stability in water or aqueous solution. Any degradation in solution that changes their physical or chemical nature can destroy their conjugation, such that their characteristic absorption (color) may be lost. Hence, dye with absorption greater than 700 nm that is water soluble and stable in aqueous solution over time would satisfy a long felt need.

BRIEF DESCRIPTION OF THE DRAWINGS

In order to better understand the present invention, some embodiments will be described below by way of non-limiting examples only, with reference to figures, wherein.

DETAILED DESCRIPTION

Figure 1:
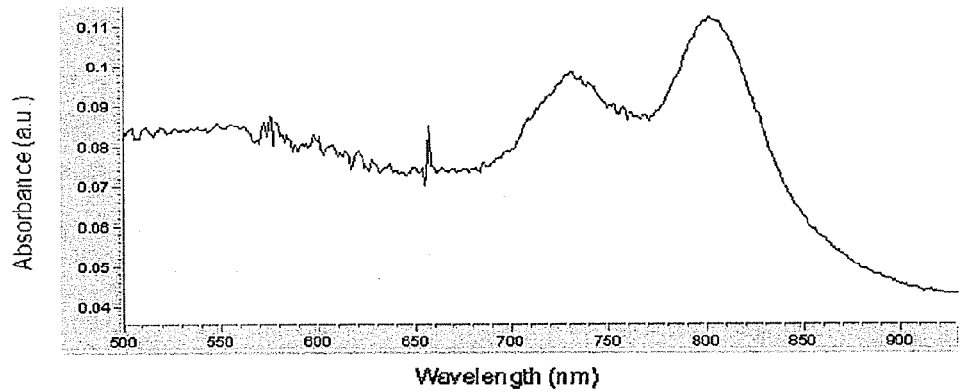
FIG. 1 represents an absorption spectrum, in water, of a naphthalocyanine dye according to one embodiment of the present invention.

Before particular embodiments of the present invention are disclosed and described, it is to be understood that the present invention is not limited to the particular process and materials disclosed herein as such and may vary to some degree. It is also to be understood that the terminology used herein is used for the purpose of describing particular embodiments only and is not intended to be limiting, as the scope of the present invention will be defined only by the appended claims and equivalents thereof. Moreover, examples herein are intended to be illustrative only and are presented for discussion purposes and not by way of limitation. For simplicity herein, no distinction is made between the term 'species' as referring to a single item (e.g., a single species, etc.) and a plurality of such items unless such a distinction is necessary for proper understanding. Further, as used herein, the article 'a' is intended to have its ordinary meaning in the patent arts, namely 'one or more'. For example, 'a substituent' generally means one or more substituents and as such, 'the substituent' means 'the substituent(s)' herein. Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of approximately 1 wt % to about 20 wt % should be interpreted to include not only the explicitly recited concentration limits of 1 wt % to about 20 wt %, but also to include individual concentrations such as 2 wt %, 3 wt %, 4 wt %, and sub-ranges such as 5 wt % to 15 wt %, 10 wt % to 20 wt %, etc. The phrase "at least" as used herein means that the number of specified items may be equal to or greater than the number recited. The phrase "about" as used herein means that the number recited may differ by plus or minus 10%; for example, "about 5" means a range of 4.5 to 5.5. The term "between" when used in conjunction with two numbers such as, for example, "between about 2 and about 50" includes both of the numbers recited. Moreover, examples herein are intended to be illustrative only and are presented for discussion purposes and not by way of limitation.

Embodiments of the present disclosure relate to naphthalocyanine dyes having extended conjugation with a near-infrared (NIR) absorption greater than 700 nm. In an embodiment, the present disclosure relates to naphthalocyanine dyes having absorptions in the range of 700 to 1000 nm; in another embodiment, in the range of 800 to 1000 nm.

In an embodiment of the present disclosure, the naphthalocyanine dyes are water soluble, dispersible in aqueous solution, dispersible in aqueous blend solutions and dispersible in solvent soluble compounds. In another embodiment, the naphthalocyanine dyes exhibit long term stability in such solutions and dispersions in a wide pH range.

Without being limited by the theory, it is believed that the solubility-dispersibility in various suspensions is attributed, in part, to water soluble substituent groups on the naphthalocyanine components of the dye. Furthermore, it is believed that the presence of multiple different substituent groups, such as alkyl, alkoxy or aryl groups, disturb the symmetry of naphthalocyanine dyes and result therefore in dyes that don't aggregate in solution. In an embodiment, in order to disturb the symmetry, mixed substituents are incorporated in the benzene rings.

Indeed, molecules having symmetrical structure can aggregate easily out of the solution. Thus, in an embodiment, the dyes according to the present disclosure have a non symmetrical structure, which disturb the symmetry, and which result then in dyes that do not aggregate in solution and that are easily soluble. Moreover, greater respective solubility and dispersibility may increase the extinction coefficient of naphthalocyanine dyes. Thus, in an embodiment, the presence of multiple different substituent groups disturbs the symmetry of naphthalocyanine dyes and result in an increase of the extinction coefficient.

The extinction coefficient defines how strongly a chemical species will absorb light at a given wavelength either per mass, per mole or per concentration. As such, an increased extinction coefficient means that a smaller quantity of the naphthalocyanine dye may be used for a desired application.

Therefore, only a minor amount of naphthalocyanine dyes, as described in the present disclosure, will be needed for the practical applications by comparison with other dyes. Thus, in an embodiment, inks containing such dyes have the benefit of being more stable and do not have any crystallization of these dyes.

In an embodiment, the present disclosure describes water soluble naphthalocyanine dye chromophores having extended conjugation with mixed substituents so that near-IR absorptions can be from 700 to 1000 nm range. Furthermore, in an embodiment, the present disclosure describes water soluble naphthalocyanine dyes that exhibit high extinction coefficient. In an embodiment, these dyes are chemically stable in water as well as in aqueous solvent blends at wide pH range and are very well suited for water based inkjet ink applications.

Without being linked by the theories, it is believed that the various substituents included in the chemical structures of the NIR-absorbing naphthalocyanine dye embodiments render the dye embodiments soluble or dispersible in either water soluble ink formulations or solvent soluble ink formulations and blends thereof. The NIR-absorbing naphthalocyanine dye embodiments of the present invention find use in many different water-based systems such as coatings & ink.

In an embodiment, a NIR-absorbing naphthalocyanine dye according to the various embodiments of the present disclosure includes solubilizing groups including, but not limited to, one or more of sulfonates, carboxylates, sulfates, phosphates, ammonium ions, ethylene oxides, propylene oxides and combinations thereof that facilitate water solubility-dispersibility and stability in solution or suspension, as mentioned above.

In an embodiment, the absorption of the naphthalocyanine dye described herein is in the near infrared (NIR) range and ranges from 700 nm to 1000 nm. In another embodiment, the extended conjugation of the naphthalocyanine dye shifts the absorption to greater than 800 nm.

In one embodiment, the present disclosure refers to a naphthalocyanine dye or to a fused naphthalocyanine dye represented by one of the general structures I to XV illustrated below. In another embodiment, the present disclosure refers to a naphthalocyanine dye represented by one of the following general structures I to IX:

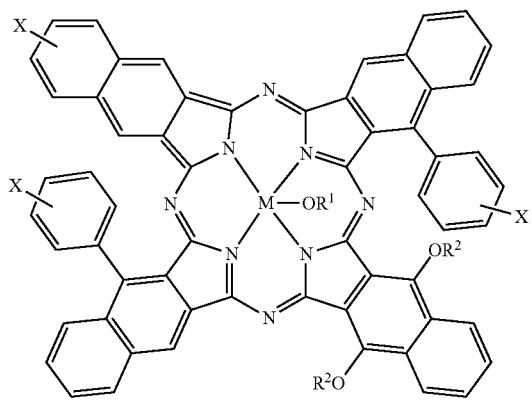
(II)

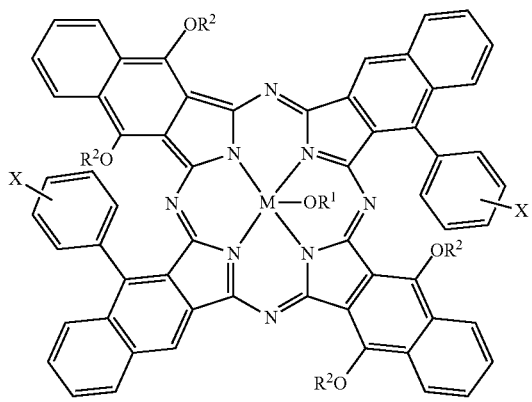
(III)

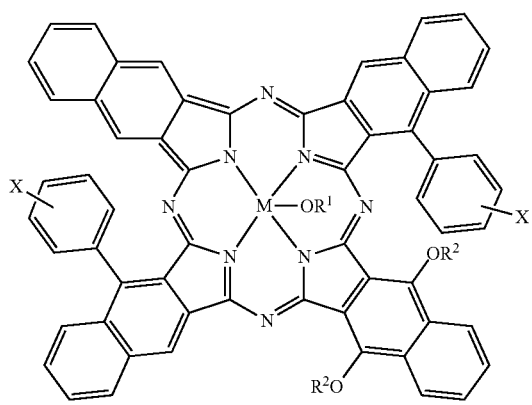
(I)

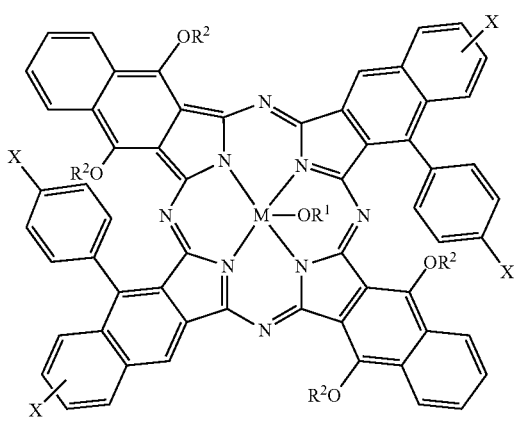
(IV)

(V)
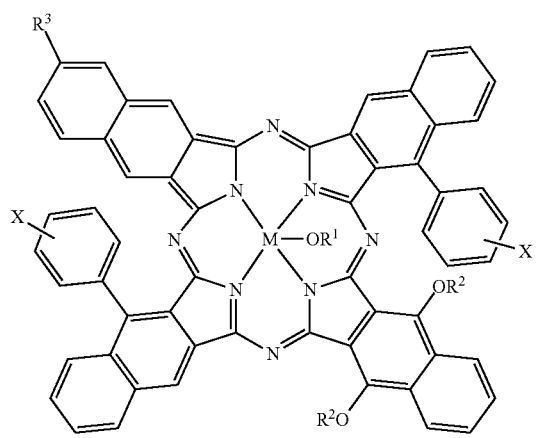
(VI)
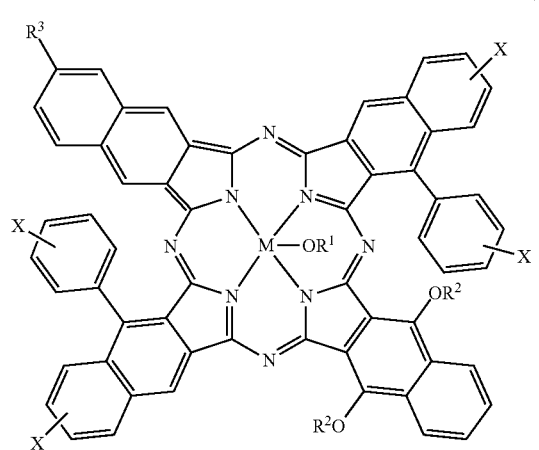
(VII)
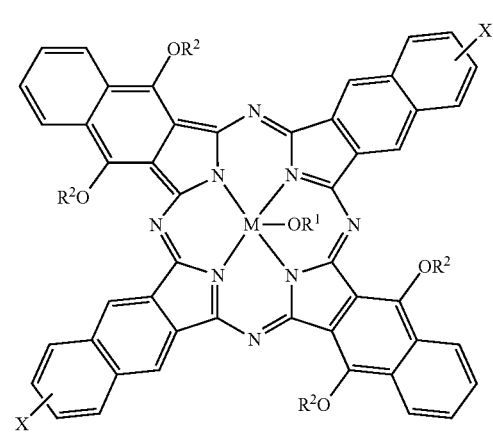
(VIII)
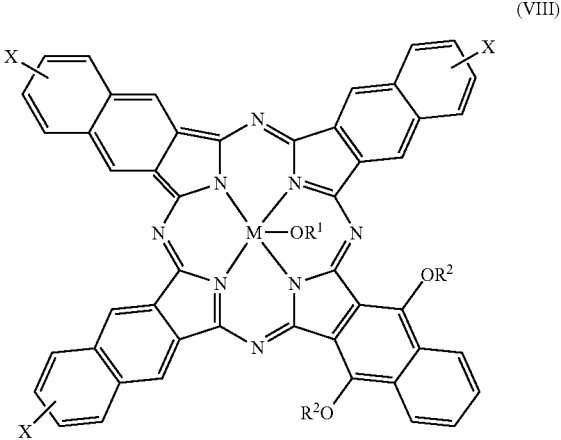
(IX)
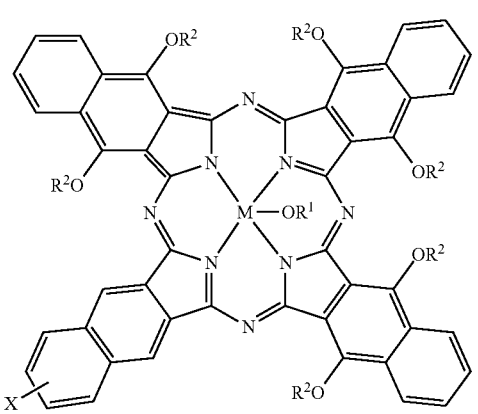
In another embodiment, the present disclosure refers to a fused naphthalocyanine dye represented by one of the general structures X to XV:

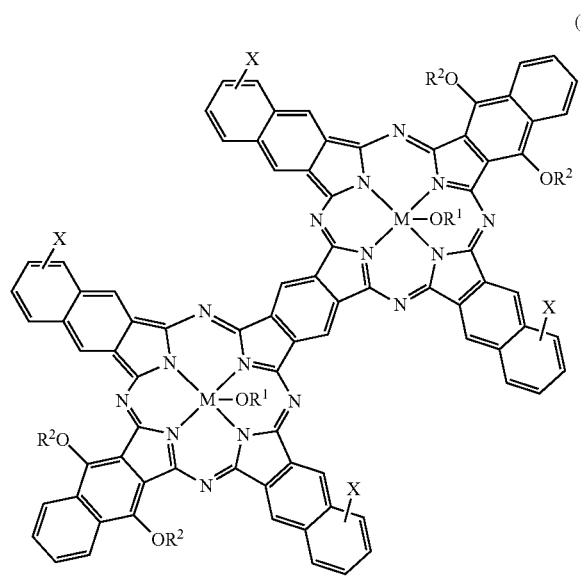
(X)
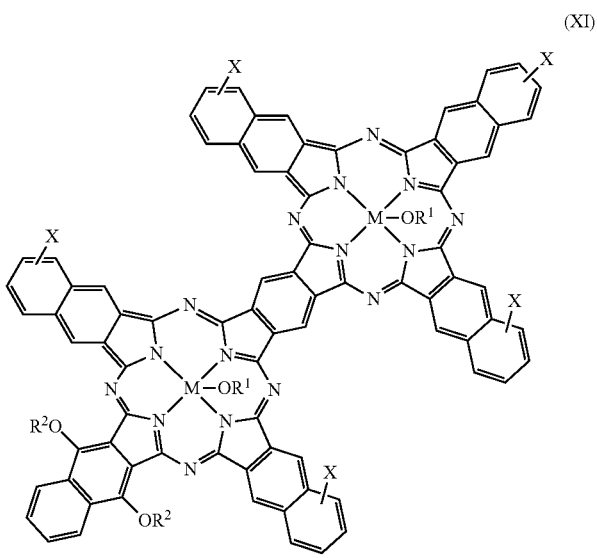
(XI)
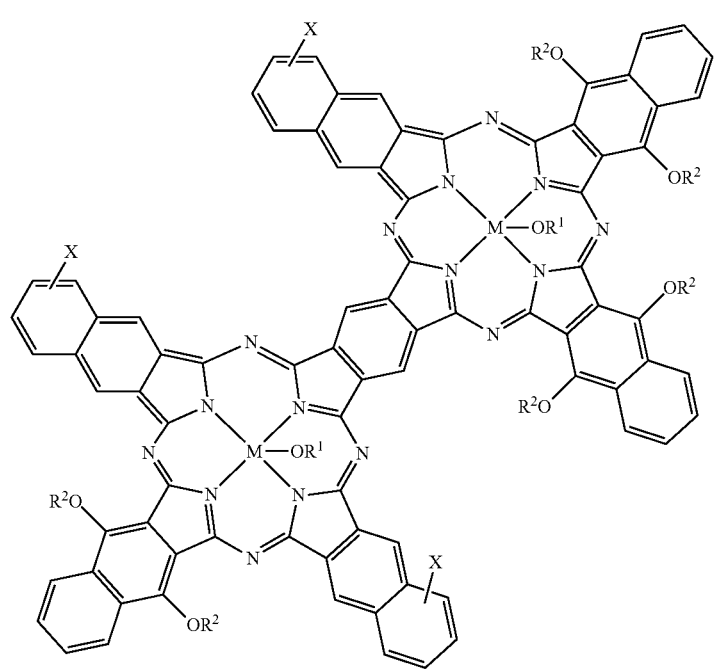
(XII)

-continued
(XIII)
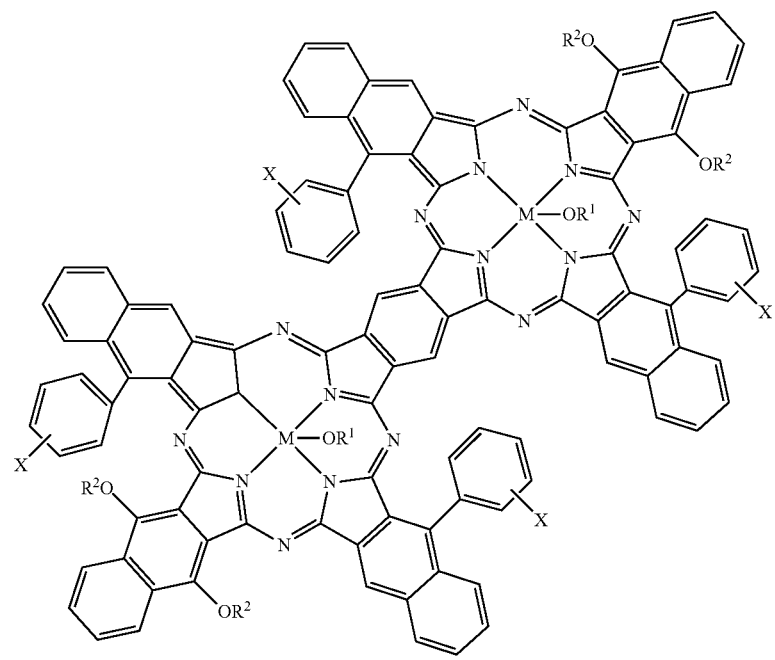
(XIV)
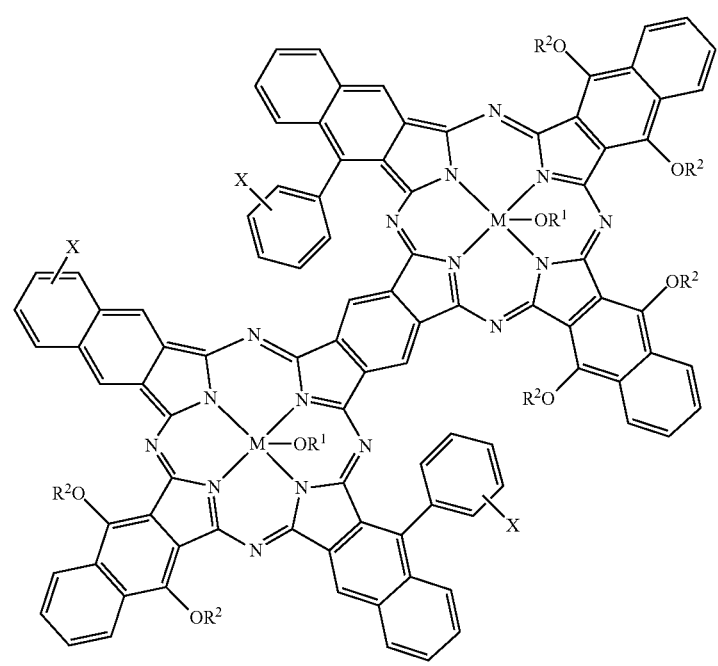

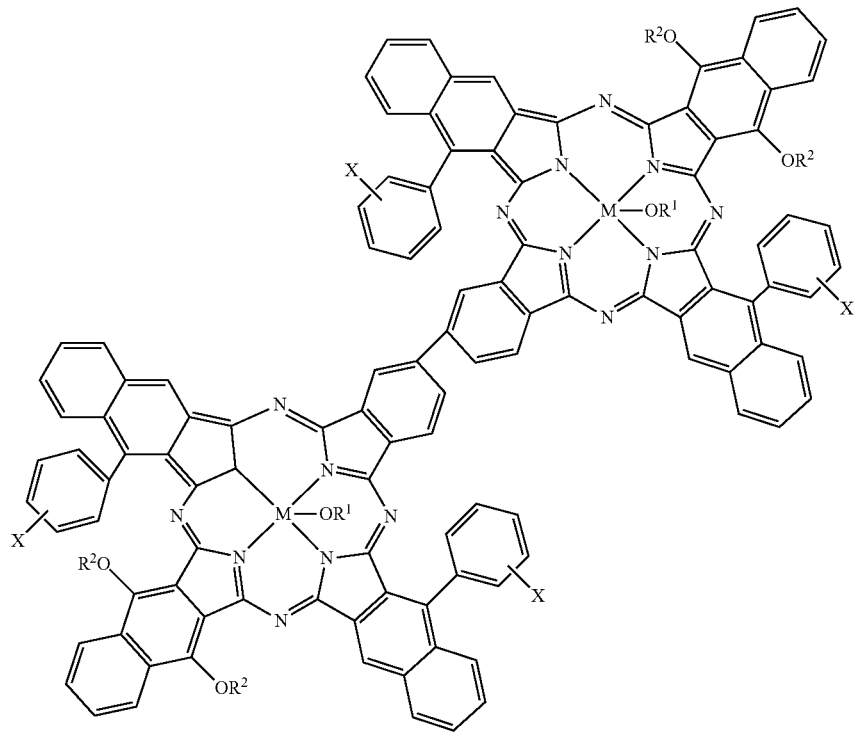

(XV)

In an embodiment, the present disclosure refers to a naphthalocyanine dye represented by one of the general structures I to IX or refers to a fused naphthalocyanine dye represented by one of the general structures X to XV, wherein, in these general structures I to XV:

$R^1$ is H or an alkyl group or a substituted alkyl group or $X^1$;

$R^2$ is, independently, Na, H, an alkyl group or a substituted alkyl group containing from 1 to 20 carbon atoms, or an aryl group or a substituted aryl group with a maximum of 5 benzene units;

$R^3$ is, independently NH$_2$, SH, an alkyl group or a substituted alkyl group containing from 1 to 20 carbon atoms, or an aryl group or a substituted aryl group with a maximum of 5 benzene units;

M is a monovalent, a divalent, a trivalent, a tetravalent or a pentavalent metal ion or transition metal ion;

X and $X^1$ are independently selected from OH, OCOR, COOZ, SO$_3$Z, PO$_3$Z$_2$, NR$_3^+$Y$^-$, and (CH$_2$CH$_2$O)$_m$CH$_3$, wherein Z is independently selected from H, a monovalent metal ion, and NR$_4^+$; wherein R is independently selected from H, an alkyl group, a substituted alkyl group, an aryl group and a substituted aryl group; wherein Y is independently selected from a halogen, sulfate, sulfonate, OH, OSO$_3$Z, and OCOR; and wherein m ranges from 1 to 500.

In an embodiment, the present disclosure refers to a naphthalocyanine dye represented by one of the following general structures I to IX wherein, in these general structures I to IX, $R^1$ is H or an alkyl group or a substituted alkyl group or $X^1$;

$R^2$ is, independently, Na, H, an alkyl group or a substituted alkyl group containing from 1 to 20 carbon atoms, or an aryl group or a substituted aryl group with a maximum of 5 benzene units;

$R^3$ is, independently, NH$_2$, SH, an alkyl group or a substituted alkyl group containing from 1 to 20 carbon atoms, or an aryl group or a substituted aryl group with a maximum of 5 benzene units;

M is a monovalent, a divalent, a trivalent, a tetravalent or a pentavalent metal ion or transition metal ion;

X and $X^1$ are independently selected from OH, OCOR, COOZ, SO$_3$Z, PO$_3$Z$_2$, NR$_3^+$Y$^-$, and (CH$_2$CH$_2$O)$_m$CH$_3$, where Z is independently selected from H, a monovalent metal ion, and NR$_4^+$; where R is independently selected from H, an alkyl group, a substituted alkyl group, an aryl group and a substituted aryl group; where Y is independently selected from a halogen, sulfate, sulfonate, OH, OSO$_3$Z, and OCOR, and where m ranges from 1 to 500.

In an embodiment of the present disclosure, the alkyl groups and substituted alkyl groups that might be present on the naphthalocyanine dye described herein are lower alkyl groups or lower substituted alkyl groups.

In an embodiment of the present disclosure, M is a monovalent, a divalent, a trivalent, a tetravalent or a pentavalent metal ion or transition metal ion. In an embodiment, when the M is a metal, the metal is a divalent, a trivalent metal, a tetravalent or a pentavalent metal complexed with the nitrogen atoms of the pyrrole moieties at the nucleus of the naphthalocyanine component. In an embodiment of the disclosure, the number of OR$^1$ group, linked with M, depends upon the valency of the metal M. Thus, in an embodiment, when the M is a trivalent metal, one linked group OR$^1$ will be present. Likewise, if the metal M is tetravalent, there will be two groups OR$^1$ of the above mentioned species. The linked OR$^1$ group provides one or more of further solubility, further dispersibility and other functionality including, but not limited to, changing the absorption range of the naphthalocyanine dye for the purposes of some embodiments of the present invention.

In an embodiment of the present disclosure, in the naphthalocyanine dye according to the general structures I to XV, and, in another embodiment, according to the general structures I to IX; M is a metal selected from the group consisting of Mg, Zn, Cd, Hg, Al, Ga, In, TI, Si, Ge, Sn, Pb, P, As, Sb, and Bi; or a transition metal is selected from the group consisting of Sc, Y, lanthanoids (La, Ce, Pr, Nd, Pm, Sm, Eu, Gd, Tb, Dy, Ho, Er, Tm, Yb, and Lu), Ti, Zr, Hf, V, Nb, Ta, Cr, Mo, W, Mn, Tc, Re, Fe, Ru, Os, Co, Rh, Ir, Ni, Pd, Pt, Cu, Ag, and Au. In another embodiment, M is a metal selected from the group consisting of In, Mn, Y, Sc, Ga, Cu, Ni, Co, Al, Mg, Fe, Sn, and Si. In yet another embodiment, the metal M is indium (In).

In an embodiment of the naphthalocyanine dyes according to the general structures I to XV, and in another embodiment, according to the general structures I to IX, $R^1$ is H or $X^1$, with $X^1$ being $SO_3Z$ and with Z being independently selected from H or a monovalent metal cation. In another embodiment, $R^1$ is H or $X^1$, with $X^1$ being $SO_3Z$ and with Z being Na, and, in yet another embodiment, $R^1$ is $SO_3Na$.

In an embodiment of the present disclosure, in the naphthalocyanine dye according to the general structures I to XV, and in another embodiment, according to the general structures I to IX, in $R^1$, $R^2$ or $R^3$, the number of carbon atoms of the alkyl or aryl group is from 1 to 20. In another embodiment, $R^2$ and $R^3$ are, independently, an alkyl group, having the formula $C_nH_{2n+1}$, wherein n range from 1 and 8. In yet another embodiment, $R^2$ and $R^3$ are, independently, an alkyl group, having the formula $C_nH_{2n+1}$, wherein n is 1 or 4.

In an embodiment of the naphthalocyanine dyes according to the general structures I to XV, and in another embodiment, according to the general structures I to IX; the substituent X group is attached to various aryl groups of the naphthalocyanine dyes. In an embodiment, the substituent group X is a soluble group that, at least, provides water solubility-dispersibility to the naphthalocyanine dyes according to embodiments of the present disclosure. Thus, in an embodiment, X is independently selected from OH, OCOR, COOZ, $SO_3Z$, $PO_3Z_2$, $NR_3^+Y^-$, and $(CH_2CH_2O)_mCH_3$, where Z is independently selected from H, a monovalent metal ion, and $NR_4^+$; where R is independently selected from H, an alkyl group, a substituted alkyl group, an aryl group and a substituted aryl group; where Y is independently selected from a halogen, sulfate, sulfonate, OH, $OSO_3Z$, and OCOR, and where m ranges from 1 to 500.

In an embodiment of the present disclosure, in the naphthalocyanine dyes according to the general structures I to XV, and in another embodiment, according to the general structures I to IX; X is $SO_3Z$, with Z being independently selected from H or a monovalent metal cation selected from the group consisting of $Na^+$, $K^+$ or $NR_4^+$, wherein R is independently selected from H, an alkyl group, a substituted alkyl group, an aryl group and a substituted aryl group. In another embodiment, X is $SO_3Z$, with Z being Na.

In an embodiment, the dye further includes water soluble substituents attached to at least one aryl group of the naphthalocyanine dye. By 'aryl group of the naphthalocyanine dye', it is meant either a benzene ring moiety (i.e., benzene moiety or benzo moiety) of the respective component or a benzene ring-derived substituent group attached to a benzene moiety of the component (e.g., a phenyl group substituent). In some embodiments, more than one water soluble groups are attached to an aryl group of the naphthalocyanine dye.

The following provides definitions for terms and phrases used above, which were not previously defined. The term "substituted" means that a hydrogen atom of a compound or moiety is replaced by another atom such as a carbon atom or a heteroatom, which is part of a group referred to as a substituent. Substituents include, for example, alkyl, alkoxy, aryl, aryloxy, alkenyl, alkenoxy, alkynyl, alkynoxy, thioalkyl, thioalkenyl, thioalkynyl, and thioaryl.

The term "heteroatom" as used herein means nitrogen, oxygen, phosphorus or sulfur. The terms "halo" and "halogen" mean a fluoro, chloro, bromo, or iodo substituent. The term "cyclic" means having an alicyclic or aromatic ring structure, which may or may not be substituted, and may or may not include one or more heteroatoms. Cyclic structures include monocyclic structures, bicyclic structures, and polycyclic structures. The term "alicyclic" is used to refer to an aliphatic cyclic moiety, as opposed to an aromatic cyclic moiety.

The phrase "aromatic ring system" or "aromatic" as used herein includes monocyclic rings, bicyclic ring systems, and polycyclic ring systems, in which the monocyclic ring, or at least a portion of the bicyclic ring system or polycyclic ring system, is aromatic (exhibits, e.g., π-conjugation). The monocyclic rings, bicyclic ring systems, and polycyclic ring systems of the aromatic ring systems may include carbocyclic rings and/or heterocyclic rings. The term "carbocyclic ring" denotes a ring in which each ring atom is carbon. The term "heterocyclic ring" denotes a ring in which at least one ring atom is not carbon and includes 1 to 4 heteroatoms.

The term "alkyl" as used herein means a branched, unbranched, or cyclic saturated hydrocarbon group, which typically, although not necessarily, contains from 1 to about 50 carbon atoms, or 1 to about 40 carbon atoms, or 1 to about 30 carbon atoms for example. Alkyls include, but are not limited to, methyl, ethyl, n-propyl, isopropyl, n-butyl, isobutyl, t-butyl, octyl, and decyl, for example, as well as cycloalkyl groups such as cyclopentyl, and cyclohexyl, for example. The term "lower alkyl" means an alkyl group having from 1 to 6 carbon atoms. The term "higher alkyl" means an alkyl group having more than 6 carbon atoms, for example, 7 to about 50 carbon atoms, or 7 to about 40 carbon atoms, or 7 to about 30 carbon atoms or more. As used herein, the term "substituted alkyl" means an alkyl substituted with one or more substituent groups. The term "heteroalkyl" means an alkyl in which at least one carbon atom is replaced with a heteroatom. If not otherwise indicated, the term "alkyl" includes unsubstituted alkyl, substituted alkyl, lower alkyl, and heteroalkyl.

The term "aryl" means a group containing a single aromatic ring or multiple aromatic rings that are fused together, directly linked, or indirectly linked (such that the different aromatic rings are bound to a common group such as a methylene or ethylene moiety). Aryl groups described herein may contain, but are not limited to, from 5 to about 50 carbon atoms, or 5 to about 40 carbon atoms, or 5 to 30 carbon atoms or more. Aryl groups include, for example, phenyl, naphthyl, anthryl, phenanthryl, biphenyl, diphenylether, diphenylamine, and benzophenone. The term "substituted aryl" refers to an aryl group including one or more substituent groups. The term "heteroaryl" means an aryl group in which at least one carbon atom is replaced with a heteroatom. If not otherwise indicated, the term "aryl" includes unsubstituted aryl, substituted aryl, and heteroaryl.

In an embodiment of the present disclosure, the naphthalocyanine as described above are prepared from the corresponding naphthalonitrile compounds with the desired stoichiometry. In an embodiment, these compounds are mixed together with all the precursors and heated to higher temperature. In an embodiment, the naphthalocyanine as described above could be further purified by column chromatography separation and/or recrystallization techniques. In an embodiment, the naphthalocyanine compounds are made in a single step synthetic process from their precursors, such as aromatic 2,3-dicyano- or 2,3-carboxylic acids or anhydrides and their corresponding metallic compounds. These compounds are made into water soluble compounds by incorporating sulfonate or other water soluble groups on the aromatic rings. Alternatively, in another embodiment, if these water soluble groups contain aromatic 2,3-dicyano- or 2,3-dicarboxylic acids or anhydrides and their corresponding metallic compounds, they can get the final water soluble form itself.

The NIR-absorbing naphthalocyanine dye embodiments of the present invention find use in water-based ink systems, for example, inkjet inks for inkjet printers, for a variety of applications including, but not limited to, print quality, print authenticity, security, print authentication, RFID tags and barcodes, for example.

In the application involving print quality of inkjet printers, an inkjet print head is used to eject ink droplets very accurately in predetermined locations on a substrate. The quantity of nozzles, in an inkjet print head, can range from several nozzles to more than 400 nozzles, each for ejecting ink droplets. As a rule of thumb, the more nozzles present in the print head, generally the better the print quality and speed. However, any of the nozzles in the print head may get blocked or clogged from time to time, possibly due to particles in the inkjet ink dispersions or dry conditions. When a nozzle is clogged or partially blocked, the ink may at least streak on the substrate, and might leave unprinted or partially printed streak mark. Streaking ink equates to poor print quality. By incorporating the NIR-absorbing naphthalocyanine dye embodiments of the present disclosure with the inkjet ink, an opportunity to monitor print quality and nozzle operation during printing is provided.

The NIR-absorbing naphthalocyanine dye according to embodiments of the present disclosure further provide opportunities to monitor and assess print authenticity, as well as other areas that use ink, because of the unique absorption range of the NIR-absorbing naphthalocyanine dye according to embodiments of the present disclosure.

In an embodiment, the present disclosure refers to an inkjet ink formulation including the naphthalocyanine dye such as defined herein, above, wherein said naphthalocyanine dye is either soluble or dispersed in the inkjet ink. The inkjet ink formulation includes an inkjet ink and a naphthalocyanine dye, such as described in the present disclosure, dispersed or dissolved in the inkjet ink. The naphthalocyanine dye is stable in the inkjet ink for a shelf life of the inkjet ink. In the inkjet ink formulation, the naphthalocyanine dye has a NIR absorption that is shifted into a range of from 700 to 1000. In another embodiment, naphthalocyanine dye has a NIR absorption that is shifted to greater than 800 nm, which is distinguishable from any absorption in the visible range of spectrum (400-750 nm) that the inkjet ink might have. The inkjet ink formulation embodiment of the present invention has numerous applications including, but not limited to print quality, as mentioned above.

In some embodiments, the inkjet ink is a water soluble inkjet ink (i.e., aqueous ink) based on a mixture of water, glycol and dyes or pigments, for example for most everyday printing applications. In other embodiments, the inkjet ink is a solvent-based ink made with volatile organic compounds (VOC). The solvent-based inks find use in printing of vinyl substrates (e.g., billboards and banners). In still other embodiments, the inkjet ink is either a UV-curable ink that includes acrylic monomers with an initiator that cured by exposure to strong UV-light or a dye sublimation ink that includes a sublimation dye and is used to print directly or indirectly on to fabrics having polyester fibers, for example. All of the inkjet inks provide a variety of colors using either the additive red-green-blue (RGB) color model or the subtractive cyan-magenta-yellow-key (CMYK) color model. In an embodiment, inkjet ink including near IR absorbing dye can be a clear ink, without any visible colorants, i.e., without any CMY colorants in it.

In an embodiment, the present disclosure refers to a printing method using inkjet ink formulation including the naphthalocyanine dye such as defined herein. In an embodiment, this method includes providing a printing system, e.g., an inkjet printer, installed with an optical sensing system, which includes an infrared light emitting diode (LED) device (illuminant) configured to emit infrared radiation that matches the spectral absorbance of the NIR naphthalocyanine dye in the inks, i.e., emits electromagnetic light energy within the near infrared spectrum, and an infrared sensor coupled to the LED device. The sensor is capable of detecting absorbance in response to illumination by the LED. At least approximate matching between the emitted electromagnetic energy and the peak absorbance of the NIR material is desired, e.g., peak absorbance of the dye within 50 nm of the infrared light energy emitted from the LED. The sensing system may be a through-page sensing system, which measures transmissive light, and in which the illuminant and the infrared sensor are positioned on opposite sides of the print medium. The sensing system may also be a reflectance-measuring system, which measures the reflected light, and in which the illuminant and the infrared sensor are positioned on the same side of the print medium. When the inks are printed on a paper, the presence of the NIR absorbing dye can be detected using the LED device coupled with the sensor as discussed above. The NIR absorbing dye absorbs some portion of the emitted light from the LED. The decrease in LED intensity is detected by the sensor, which then registers the presence of the NIR dye. By adding a sufficient amount of NIR absorbing dye to the inks, a method of detection can be provided that is independent of the ink colors.

In another embodiment of the present disclosure, a detection system for a NIR-absorbing naphthalocyanine dye with extended conjugation is provided. The detection system provides detection of the naphthalocyanine dye in a variety of applications, as mentioned above from print quality to print authentication, for example. In some embodiments, the detection system is incorporated into an inkjet printer.

Figure 3:
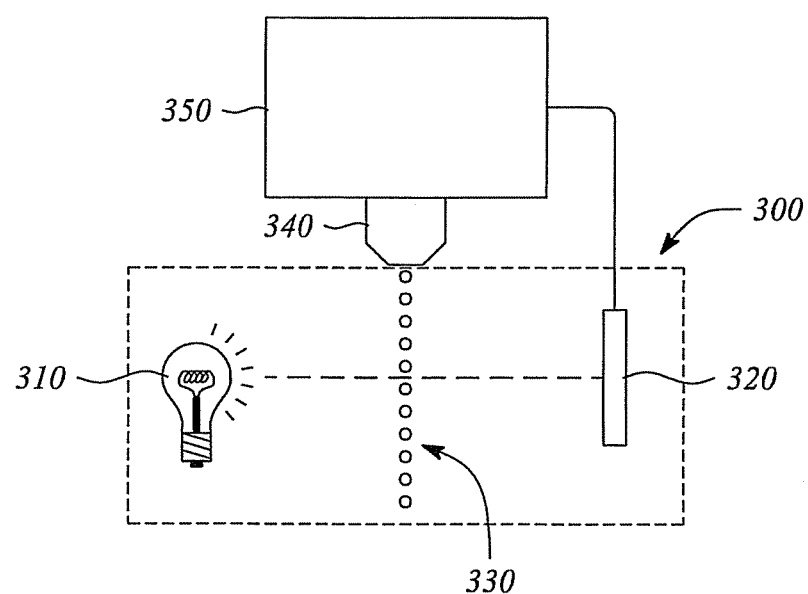
FIG. 3 illustrates a block diagram of a detection system for an inkjet printer, according to an embodiment of the present invention.

FIG. 3 illustrates a block diagram of a detection system 300 for an inkjet printer according to an embodiment of the present invention. In an embodiment, the detection system 300 includes an NIR illumination source 310 that emits infrared light at a wavelength between 700 nm and 1000 nm. The NIR illumination source 310 may be light emitting diode (LED), for example. In an embodiment, the detection system 300 further includes an NIR sensor 320 that detects the infrared light from the NIR illumination source 310. The NIR sensor 320 may be a photodiode that detects radiation between 700 nm and 1000 nm of wavelength, for example. The detection system 300 further includes a medium 330 that includes an NIR-absorbing naphthalocyanine dyes such as described in the present disclosure. In the embodiment illustrated in FIG. 3, the medium 330 is an inkjet ink 330. In another embodiment, the medium 330 can be a media substrate on which the inkjet ink including NIR-absorbing naphthalocyanine dyes is printed on. The inkjet ink 330 includes naphthalocyanine dyes such as described in the present disclosure dispersed in the inkjet ink 330. As such, the inkjet ink 330 absorbs light in the NIR range. In an embodiment, the inkjet ink 330 absorbs light at greater than 800 nm. In an embodiment, the inkjet ink 330 is dispensed through a nozzle 340 of an inkjet print head of an inkjet printer 350. The NIR illumination source 310 is directed at an output path of the nozzle 340 to illuminate the inkjet ink 330 that is dispensed by the nozzle 340. The NIR sensor 320 is directed at the output path and the illumination path.

According to embodiments of the present disclosure, in an example of detecting print quality from the inkjet printer 350, when the nozzle 340 of the inkjet print head is operating efficiently, the inkjet ink 330 emanates from the nozzle output in the output path. The light from the illumination source 310 is absorbed by the naphthalocyanine dye in the inkjet ink 330 and the NIR sensor 320 does not detect a change in the light (or a change in an amount of light) from the illumination source 310. When the nozzle 340 becomes clogged, whether due to the inkjet ink 330 inside the nozzle 340 drying up or for another reason, little or no inkjet ink 330 is dispensed by the nozzle 340. The light from the NIR illumination source 310 is no longer absorbed if the inkjet ink 330 is not dispensed from the nozzle output. As such, NIR sensor 320 begins detecting the light (e.g., detects a change in either the light or an amount of the light) from the NIR illumination source 310. The detected light by the NIR sensor 320 triggers the NIR sensor 320 to communicate to the inkjet printer 350 that the nozzle 340 is not operating correctly. The inkjet printer 350 uses the communication from the NIR sensor 320 to compensate for the clogged nozzle 340, such that print quality from the inkjet printer is maintained.

The following examples illustrate a number of embodiments of the present systems and methods that are presently known. However, it is to be understood that the following are only exemplary or illustrative of the application of the principles of the present systems and methods. Numerous modifications and alternative compositions, methods, and systems may be devised by those skilled in the art without departing from the spirit and scope of the present systems and methods. The appended claims are intended to cover such modifications and arrangements. Thus, while the present systems and methods have been described above with particularity, the following examples provide further detail in connection with what are presently deemed to be the acceptable embodiments.

Example 1

Table A below illustrates some naphthalocyanine dyes according to embodiments of the present invention:

TABLE A

1) 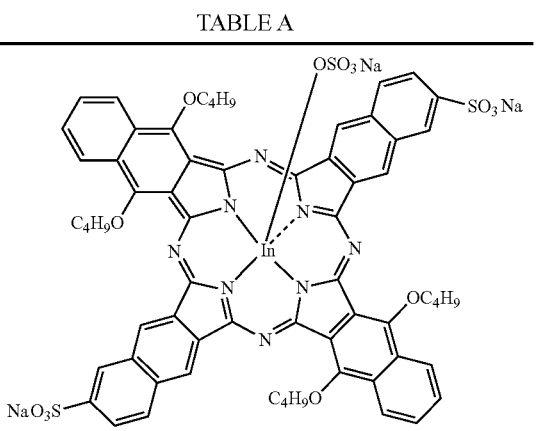

2) 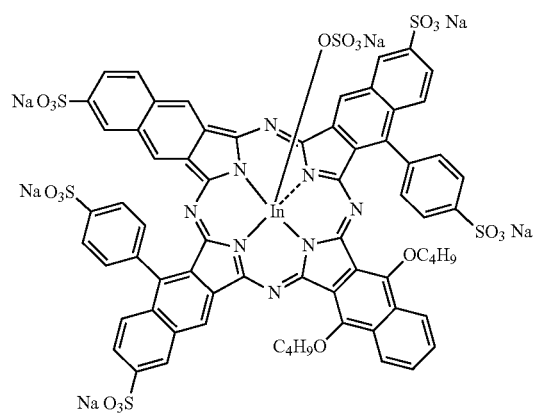

TABLE A-continued

3) 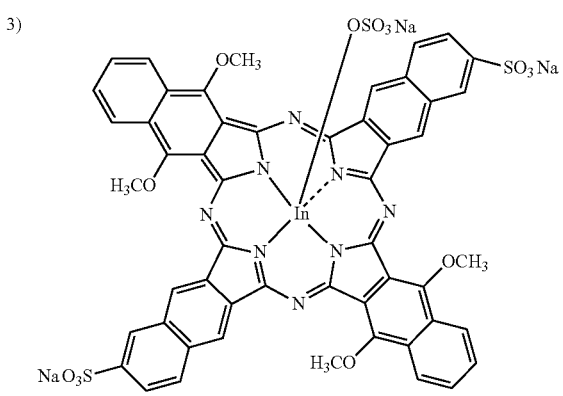

4) 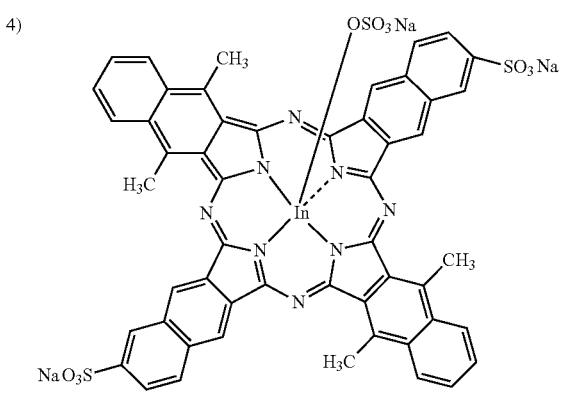

5) 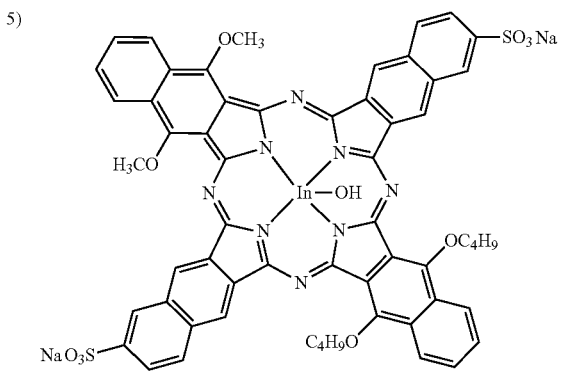

TABLE A-continued
6)
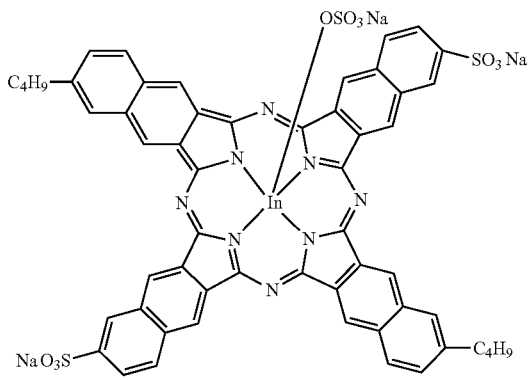
7)
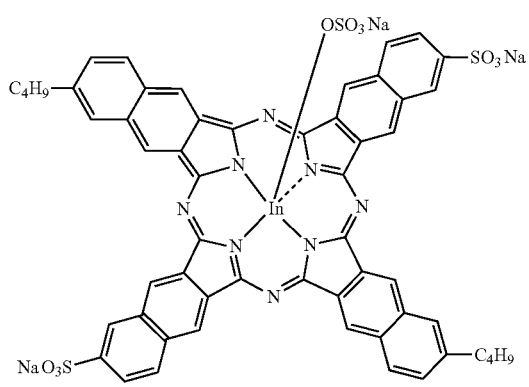
8)
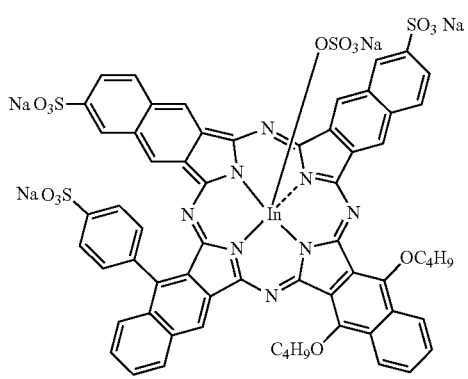
9)
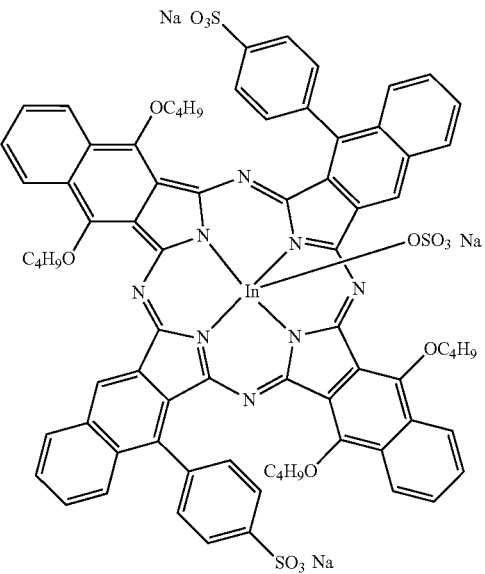
10)
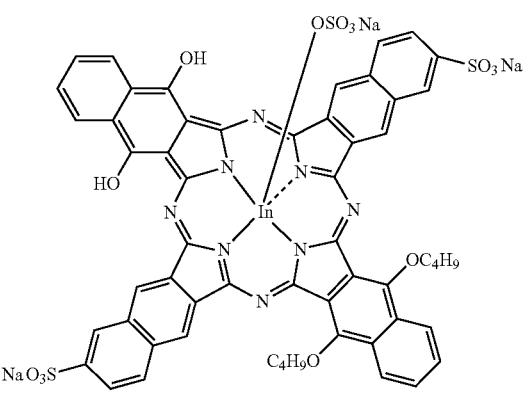
11)
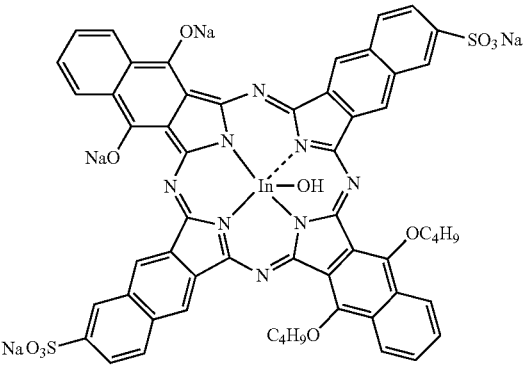

TABLE A-continued
12) 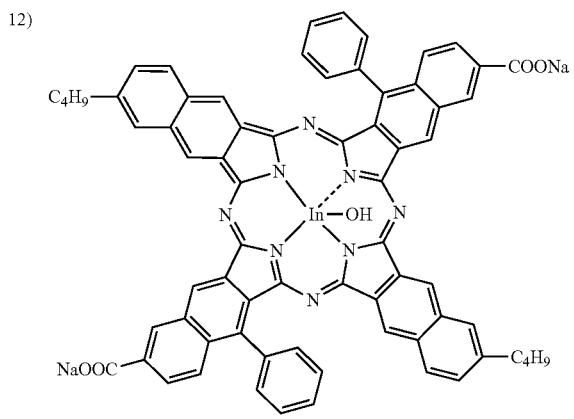
13) 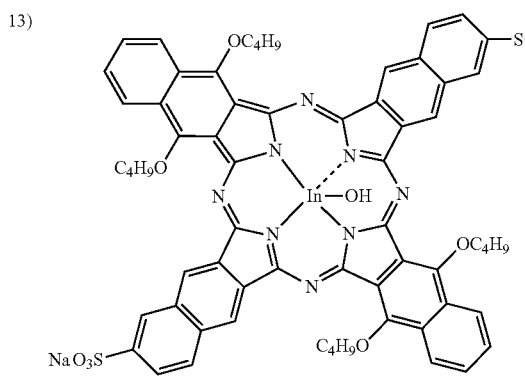
14) 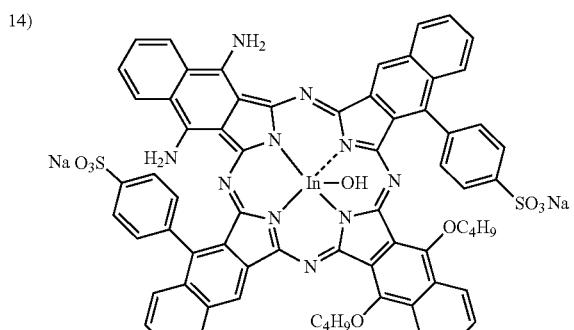
15) 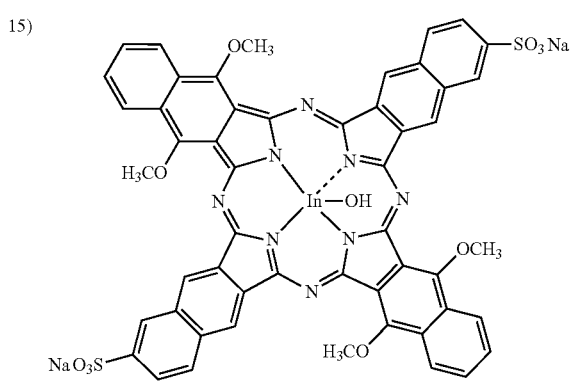
16) 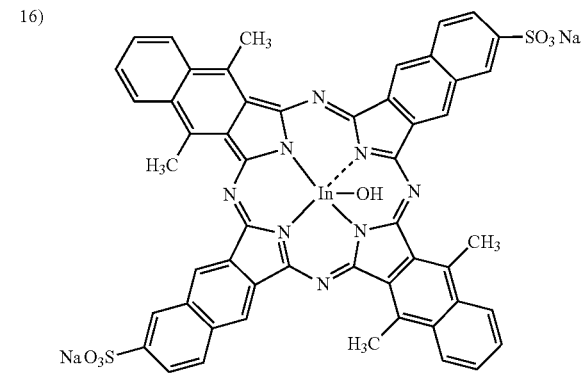
17) 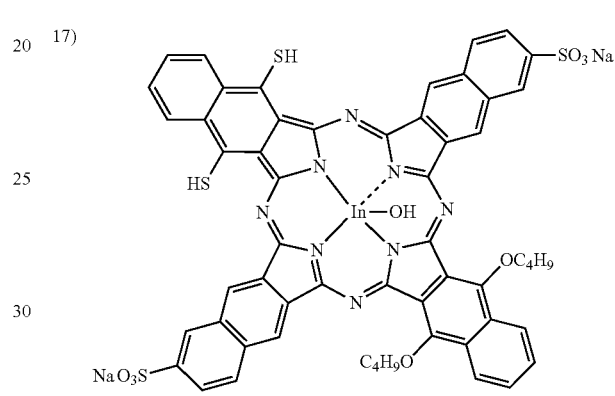
18) 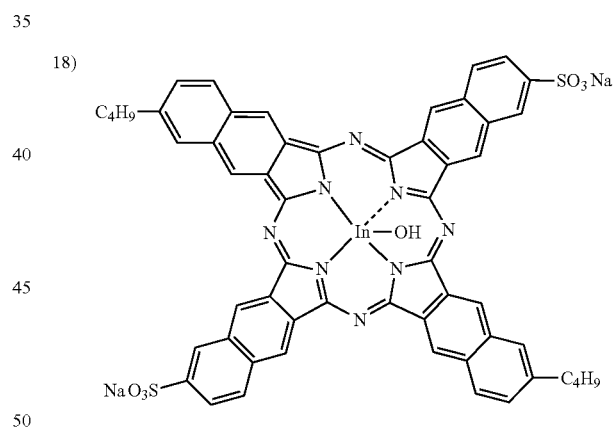
19) 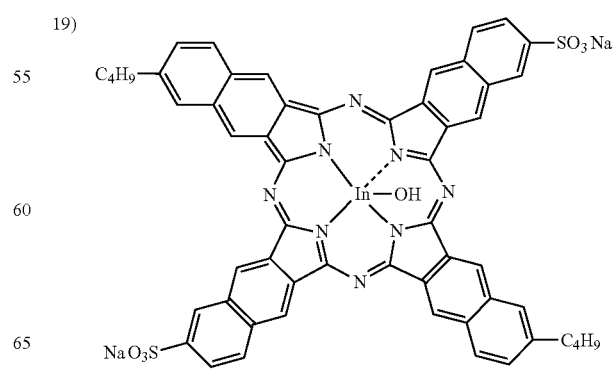

TABLE A-continued

20)
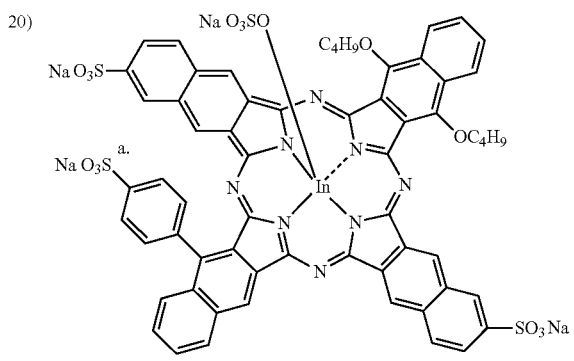

21)
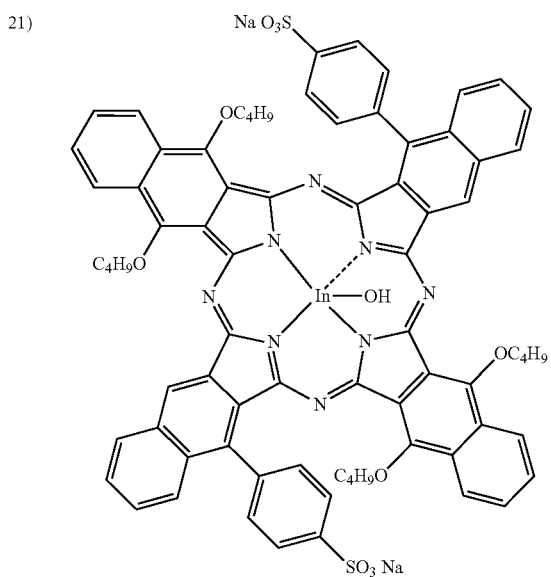

22)
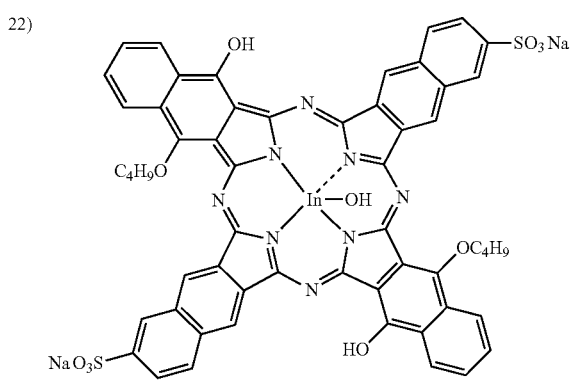

TABLE A-continued

23)
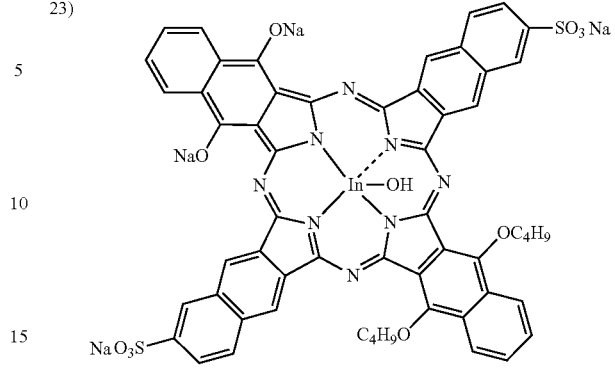

Example 2

A naphthalocyanine dye including, in particular, an indium naphthalocyanine sulfonate sodium salt is formulated. The naphthalocyanine compound has the chemical structure (VII), wherein $R^1$ and X are $SO_3Na$, wherein $R^2$ is $CH_2CH_2CH_2CH_3$ and wherein M is In.

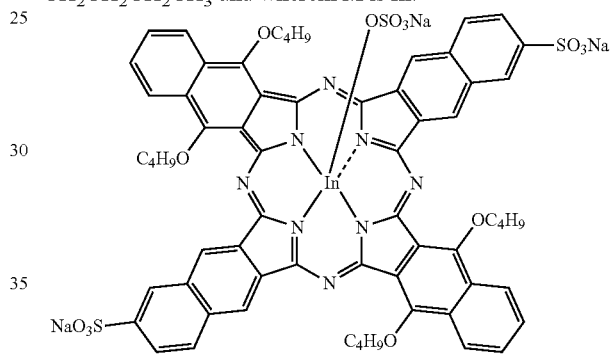

To make the naphthalocyanine compound of the example 2 above, 2.58 gram of 1,4-Dibutoxy-2,3-naphthalenedicarbonitrile; 1.42 grams of 2,3-naphthalenedicarbonitrile and 1.17 grams of indium acetate are mixed with 3.2 g urea along with a catalytic quantity of ammonium molybdate (0.12 g). This mixture is then heated to 210° C. for 2.5 hours. This mixture is then cooled and washed with water followed by a wash with isopropanol to obtain the product with naphthalocyanine ring having mixed substituents. Those mixed groups are the naphthalene having hydrogen and butoxy units. This product (5.2 g) is sulfonated with fuming sulfuric acid containing 20% of sulfur trioxide (21 ml) at ambient temperature for two days. During this step, some degree of cleavage of ether groups is possible to obtain a mixture of groups such as hydroxy and butoxy units on the naphthyl ring. Then, the mixture is poured in crushed ice and the precipated product is filtered to obtain the product in the acid form. The resulting product is neutralized with 50% sodium carbonate solution to a pH of 7.1 and is dialyzed against water to remove any inorganic salts. Water is then removed to obtain water soluble sulfonate groups attached to the naphthalene rings with a yield of 4.0 g. FIG. 1 illustrates the absorption spectrum, in water, of the dye obtained according to example 2.

Example 3

A naphthalocyanine dye including, in particular, an indium tetraphenyl naphthalocyanine sulfonate sodium salt is formulated. The naphthalocyanine compound has the chemical structure (X), wherein $R^1$ and X are $SO_3Na$, wherein $R^2$ is $CH_2CH_2CH_2CH_3$ and wherein M is In.

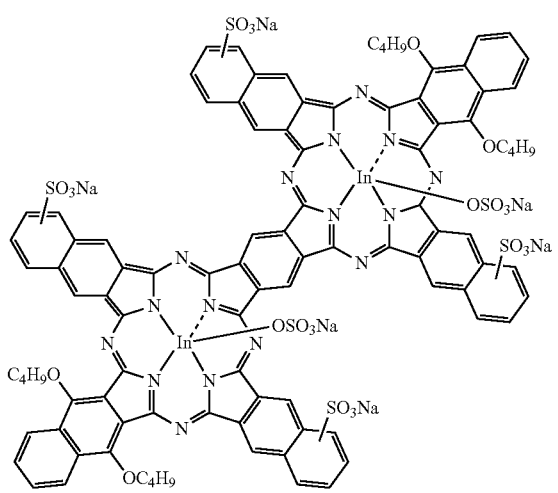

Figure 2:
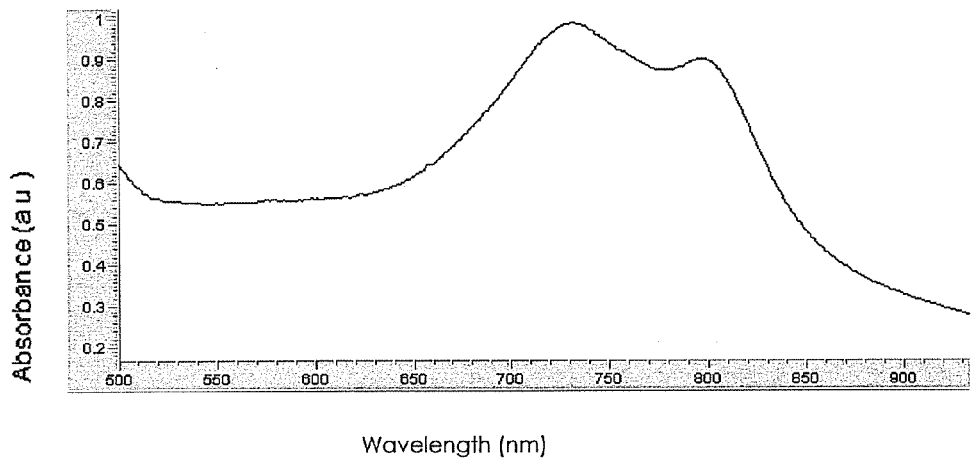
FIG. 2 represents an absorption spectrum, in water, of a naphthalocyanine dye according to another embodiment of the present invention.

To make the fused naphthalocyanine compound of example 3, 1,4-Dibutoxy-2,3-naphthalenedicarbonitrile (1.77 g), 2,3-naphthalenedicarbonitrile (1.45 g), 1,2,4,5-tetracyanobenzene (0.44 g), indium acetate (1.45 g) are mixed with urea (4.0 g) along with a catalytic quantity of ammonium molybdate (0.1 g). This mixture is heated to 210° C. for 2 hours. This mixture is then cooled and washed with water followed by isopropanol to obtain the product with fused naphthalocyanine ring having mixed substituents. Those mixed groups are the naphthalene having hydrogen and butoxy units. This product (5.7 g) is sulfonated with fuming sulfuric acid containing 20% sulfur trioxide (23 ml) at ambient temperature for 24 hours. During this step, some degree of cleavage of ether groups is possible to obtain a mixture of groups such as hydroxy and butoxy units on the naphthyl ring. Then, the mixture is poured in crushed ice and the precipated product is filtered to obtain the product in the acid form. The resulting product is then neutralized with sodium carbonate to a pH of 7.1 and dialyzed against water to remove any inorganic salts. Water is removed to obtain water soluble sulfonate groups attached to the naphthalene rings. FIG. 2 illustrates the absorption spectrum, in water, of the dye obtained according to example 3.

Example 4

A naphthalocyanine compound having the chemical structure (IX), where $R^1$ and X are $SO_3Na$, where $R^2$ is $CH_2CH_2CH_2CH_3$, and where M is In, is formulated.

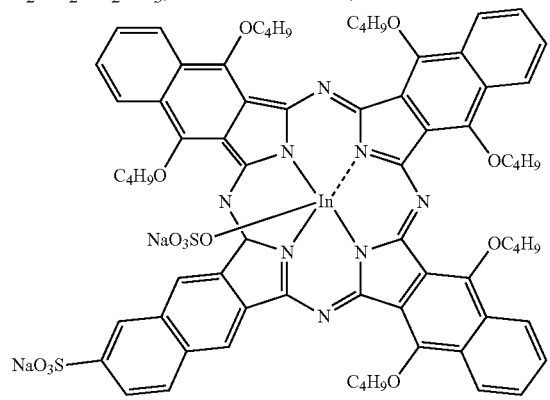

To make the naphthalocyanine compound according to example 4, 3.87 gram of 1,4-Dibutoxy-2,3-naphthalenedicarbonitrile; 0.71 grams of 2,3-naphthalenedicarbonitrile and 1.17 grams of indium acetate are mixed with 3.2 g urea along with a catalytic quantity of ammonium molybdate (0.12 g). This mixture is heated to 210° C. for 2.5 hour. This mixture is then cooled and washed with water followed a wash with isopropanol to obtain the product with naphthalocyanine ring having mixed substituents. Those mixed groups are the naphthalene having hydrogen and butoxy units. This product is sulfonated with fuming sulfuric acid containing 20% of sulfur trioxide (7 ml) at ambient temperature for two days. Then, the mixture is poured in crushed ice and the precipated product is filtered to obtain the product in the acid form. The resulting product is neutralized with 50% sodium carbonate solution to a pH of 7.1 and is dialyzed against water to remove any inorganic salts. Water is removed to obtain water soluble sulfonate groups attached to the naphthalene rings

Example 5

A naphthalocyanine compound having the chemical structure (VIII), where $R^1$ and X are $SO_3Na$, where $R^2$ is $CH_2CH_2CH_2CH_3$, and where M is In, is formulated.

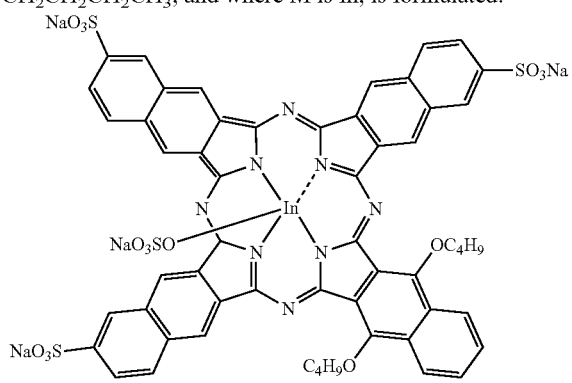

To make the naphthalocyanine compound according to example 5, 1.29 gram of 1,4-Dibutoxy-2,3-naphthalenedicarbonitrile; 2.13 grams of 2,3-naphthalenedicarbonitrile and 1.17 grams of indium acetate are mixed with 3.2 g urea along with a catalytic quantity of ammonium molybdate (0.12 g). This mixture is then heated to 210° C. for 2.5 hour. This mixture is then cooled and washed with water followed by a wash with isopropanol to obtain the product with naphthalocyanine ring having mixed substituents. Those mixed groups are the naphthalene having hydrogen and butoxy units. This product (5.2 g) is sulfonated with fuming sulfuric acid containing 20% of sulfur trioxide (21 ml) at ambient temperature for two days. Then, the mixture is poured in crushed ice and the precipated product is filtered to obtain the product in the acid form. The resulting product is neutralized with 50% sodium carbonate solution to a pH of 7.1 and is dialyzed against water to remove any inorganic salts. Water is removed to obtain water soluble sulfonate groups attached to the naphthalene rings

Example 6

Example of Ink Formula

An ink composition, containing the naphthalocyanine dye obtained according to example 2 was prepared using the components and ranges shown in Table 1. The formula is expressed in weight percentage (wt %) of each component in the ink composition.

TABLE 1

| Ingredients | Wt % |
| --- | --- |
| Surfynol SEF | 0.60% |
| 1-(2-Hydroxyethyl)-2-pyrrolidone | 8.00% |
| 1,6-Hexanediol | 3.00% |
| LEG-1 | 2.00% |
| Tetraethylene glycol | 3.00% |
| 2-Pyrrolidinone | 7.00% |
| Proxel ® GXL | 0.10% |
| Joncryl ® 683 (K salt) | 0.20% |
| Crodafos ® N-3 acid | 1.00% |
| Zonyl ® FSO | 0.10% |
| IJX ® 635E | 3.25% |
| NIR Dye according to example 2 | 0.5% |
| Water | Up to 100% |

Surfynol ® is a surfactant available from Air Products. Joncryl ® 683 is an acrylic resin is available from Johnson Wax. Proxel ® GXL is a Biocide available from Zeneca. Crodafos ® N-3 acid is available from Croda Inc. Zonyl ® FSO is a fluorosurfactants available from Dupont Inc. IJX ® 635E is a yellow pigment available from Cabot. LEG-1 is ethyloxated glycerol derivative with high molecular weight available from Lipo chemical, Inc.

All amounts in grams and milliliters (ml) mentioned above for each example are approximate and not intended as a limitation herein. Moreover, sodium counter-ions are provided by way of example. Thus, there have been described embodiments of an NIR-absorbing naphthalocyanine dye. Further, embodiments of an inkjet ink and a detection system that employ the naphthalocyanine dye have been described. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims. Many modifications and variations are possible in light of the above teaching. It is intended that the scope of the invention be defined by the following claims.

What is claimed is:

1. A naphthalocyanine dye represented by one of the general structures I to XV:

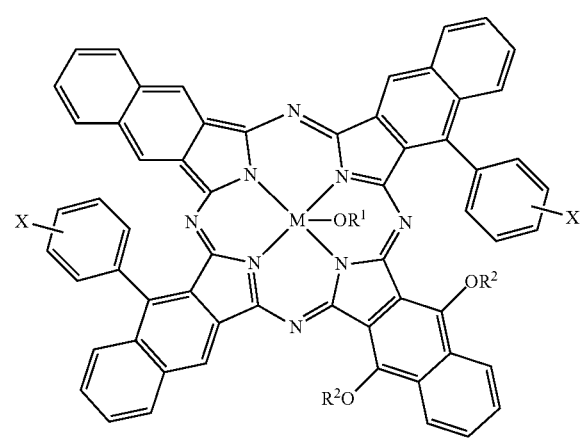

(I)

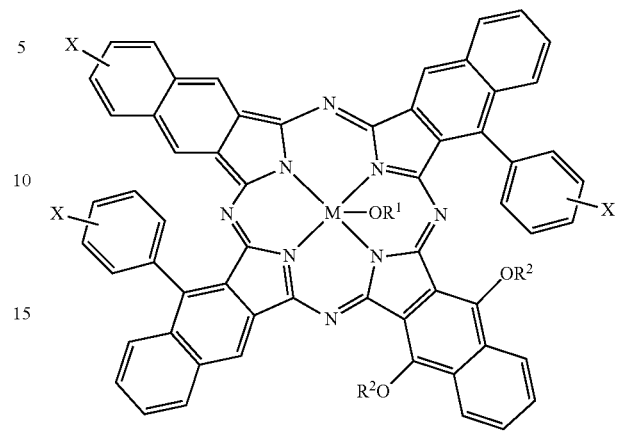

(II)

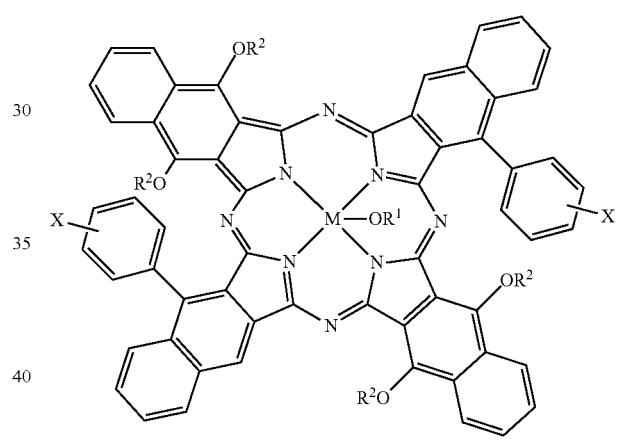

(III)

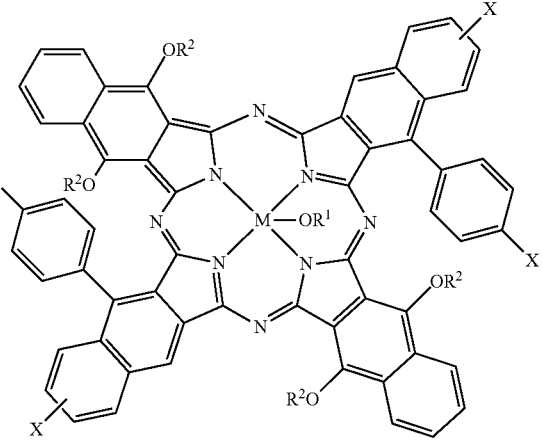

(IV)

(V)
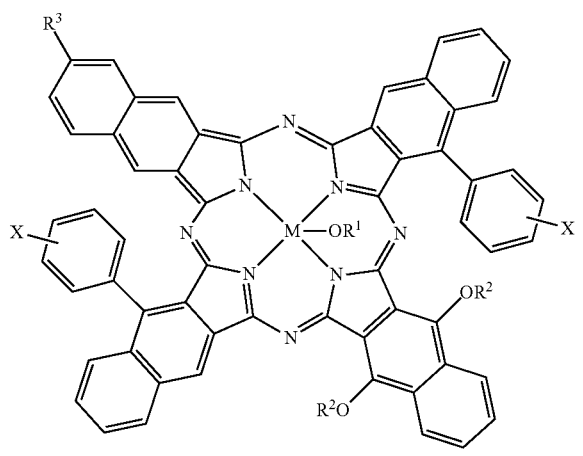
(VI)
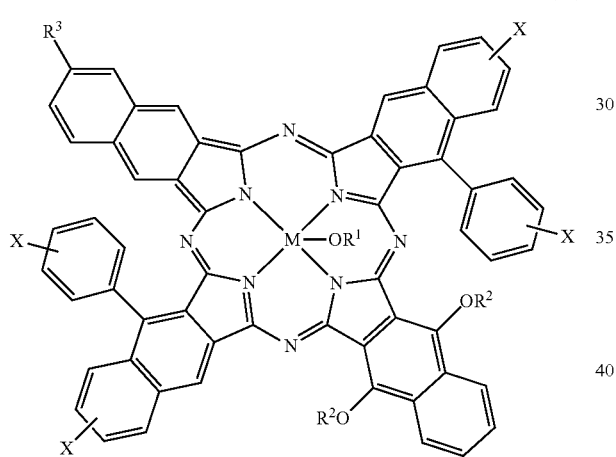
(VII)
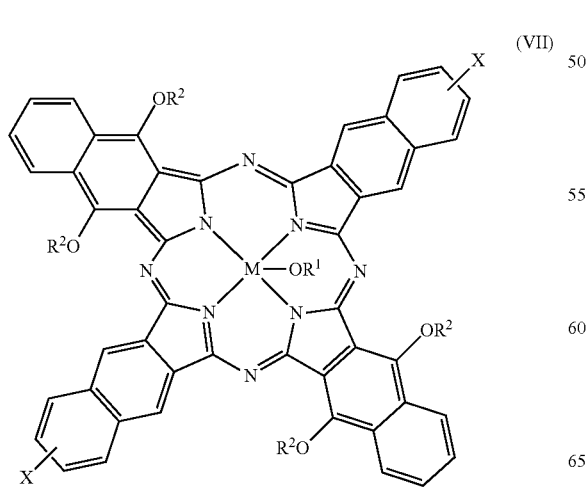
(VIII)
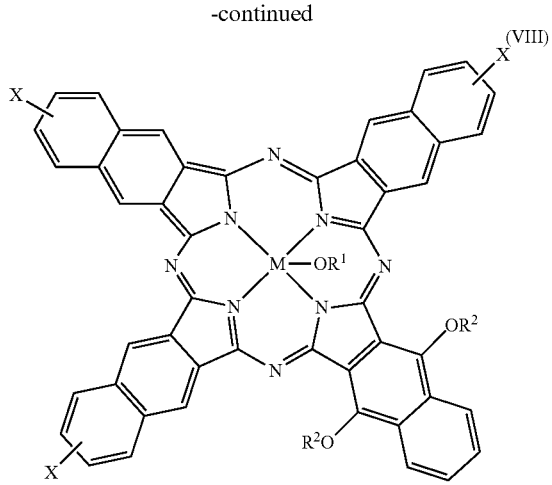
(IX)
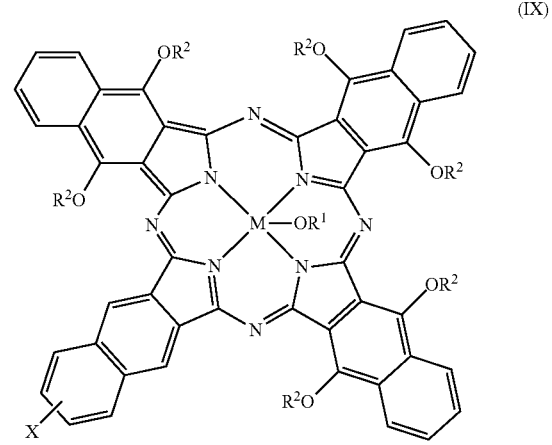
(X)
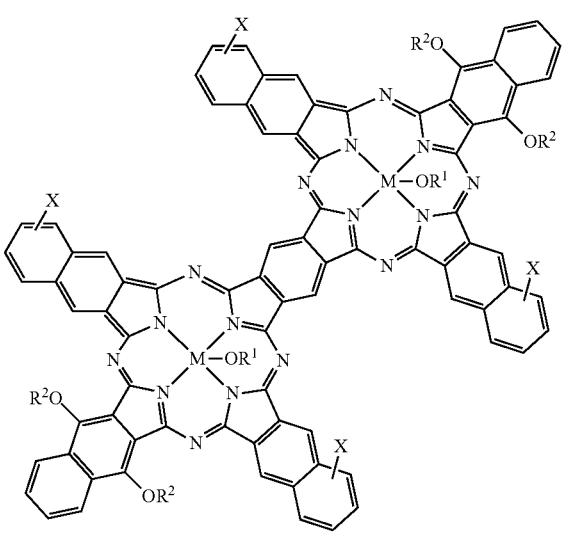

(XI)
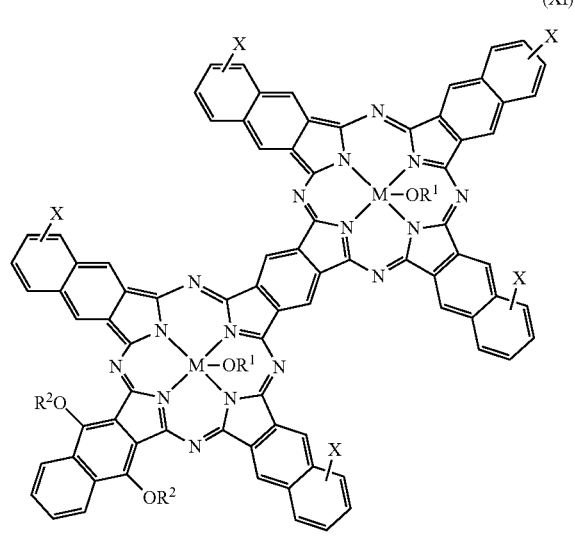

(XII)
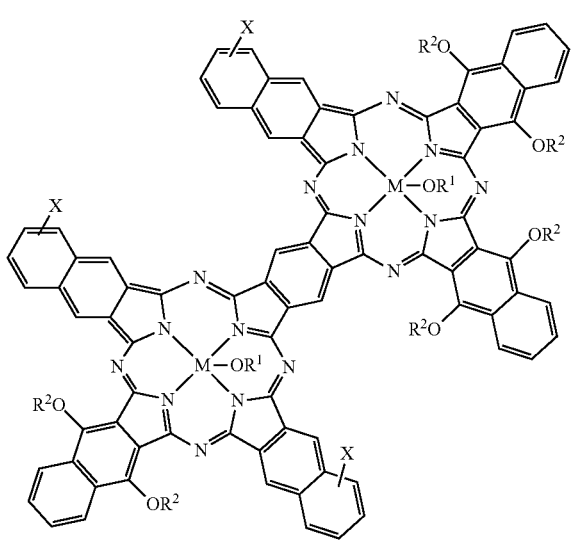

(XIII)
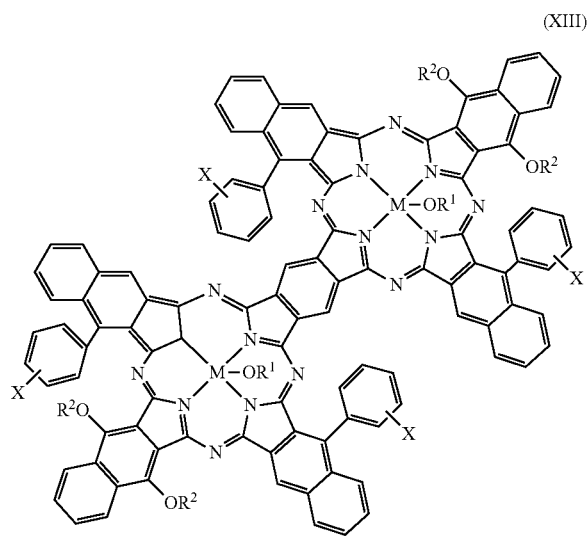

(XIV)
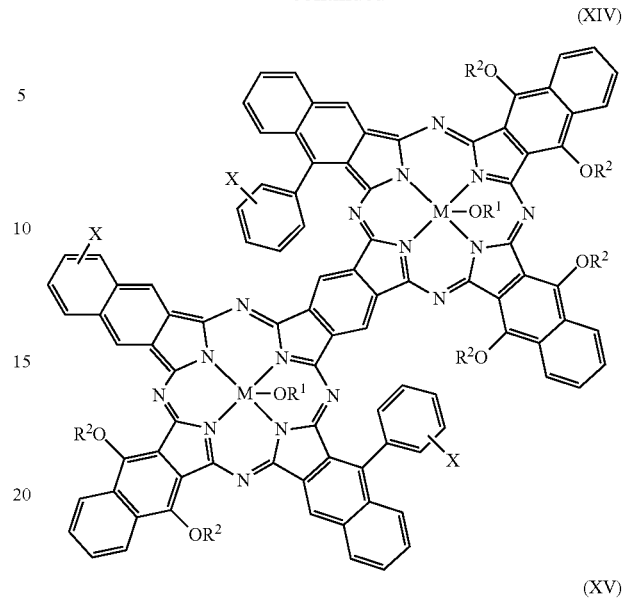

(XV)
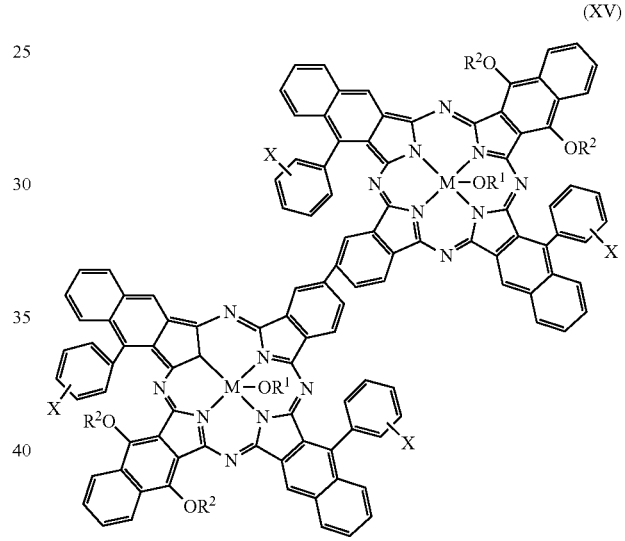

wherein:
$R^1$ is H or an alkyl group or a substituted alkyl group or $X^1$;
$R^2$ is, independently, Na, H, an alkyl group or a substituted alkyl group containing from 1 to 20 carbon atoms; or an aryl group or a substituted aryl group with a maximum of 5 benzene units;
$R^3$ is, independently, $NH_2$, SH, an alkyl group or a substituted alkyl group containing from 1 to 20 carbons atoms; or an aryl group or a substituted aryl group with a maximum of 5 benzene units;
M is a monovalent, a divalent, a trivalent, a tetravalent or a pentavalent metal ion or transition metal ion;
X and $X^1$ are, independently, selected from the group consisting of OH, OCOR, COOZ, $SO_3Z$, $PO_3Z_2$, $NR_3^+Y^-$, and $(CH_2CH_2O)_mCH_3$, wherein Z is independently selected from the group consisting of H, a monovalent metal ion, and $NR_4^+$; wherein R is independently selected from the group consisting of H, an alkyl group, a substituted alkyl group, an aryl group and a substituted aryl group; wherein Y is independently selected from the group consisting of a halogen, sulfate, sulfonate, OH, $OSO_3Z$, and OCOR, and wherein m ranges from 1 to 500.

2. A naphthalocyanine dye represented by one of the general structures I to IX:
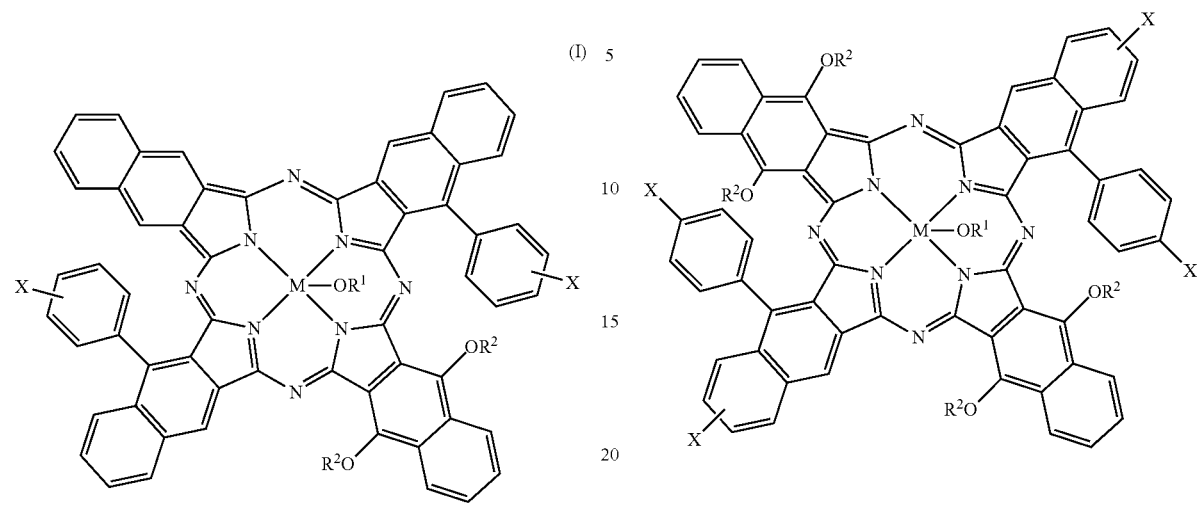
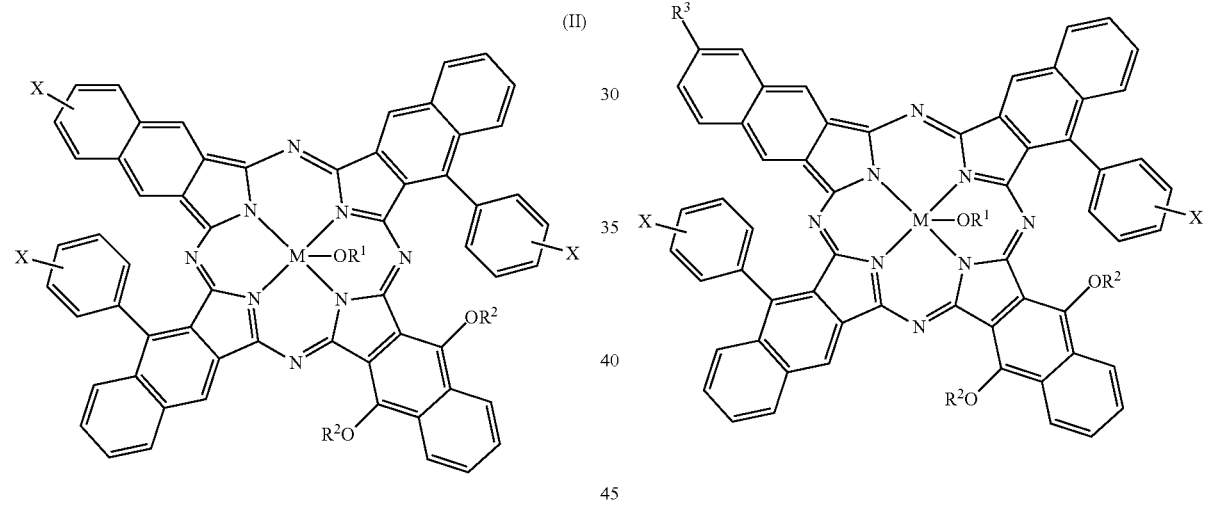
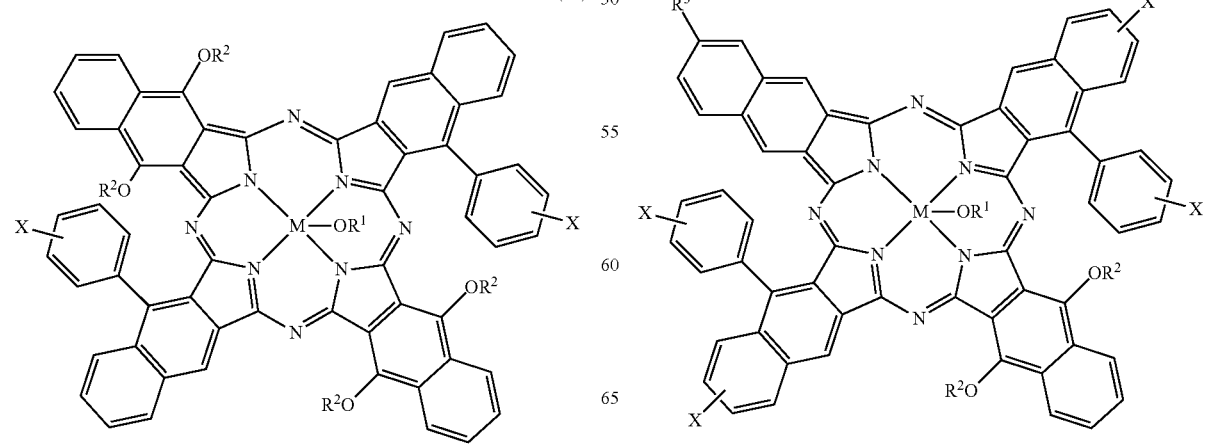

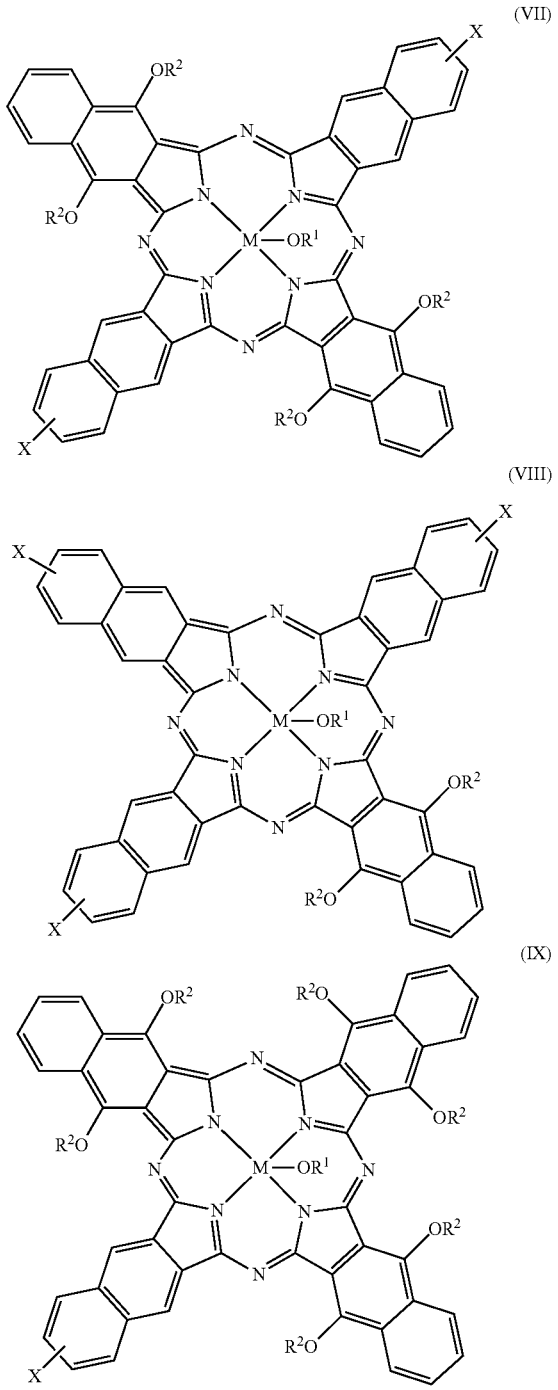

wherein
R¹ is H or an alkyl group or a substituted alkyl group or X¹;
R² is, independently, Na, H, an alkyl group or a substituted alkyl group containing from 1 to 20 carbon atoms; or an aryl group or a substituted aryl group with a maximum of 5 benzene units;
R³ is, independently, $NH_2$, SH, an alkyl group or a substituted alkyl group containing from 1 to 20 carbon atoms; or an aryl group or a substituted aryl group with a maximum of 5 benzene units;
M is a monovalent, a divalent, a trivalent, a tetravalent or a pentavalent metal ion or transition metal ion;
where X and X¹ are, independently, selected from the group consisting of OH, OCOR, COOZ, $SO_3Z$, $PO_3Z_2$, $NR_3^+Y^-$, and $(CH_2CH_2O)_mCH_3$; wherein Z is independently selected from the group consisting of H, a monovalent metal ion, and $NR_4^+$; wherein R is independently selected from the group consisting of H, an alkyl group, a substituted alkyl group, an aryl group and a substituted aryl group; wherein Y is independently selected from the group consisting of a halogen, sulfate, sulfonate, OH, $OSO_3Z$, and OCOR; and wherein m ranges from 1 to 500.

3. The naphthalocyanine dye according to claim 1 wherein R¹ is H or X¹, with X¹ being $SO_3Z$ and with Z being independently selected from the group consisting of H and a monovalent metal cation.

4. The naphthalocyanine dye according to claim 1 wherein R¹ is H or X¹, with X¹ being $SO_3Z$ and with Z being Na.

5. The naphthalocyanine dye according to claim 1 wherein R¹ is $SO_3Na$.

6. The naphthalocyanine dye according to claim 1 wherein in R¹, R² or R³, the number of carbon atoms of the alkyl or aryl group is from 1 to 20.

7. The naphthalocyanine dye according to claim 1 wherein R² and R³ are, independently, an alkyl group, having the formula $C_nH_{2n+1}$, wherein n range from 1 and 8.

8. The naphthalocyanine dye according to claim 1 wherein R² and R³ are, independently, an alkyl group, having the formula $C_nH_{2n+1}$, wherein n is 1 or 4.

9. The naphthalocyanine dye according to claim 1 wherein M is a metal selected from the group consisting of Mg, Zn, Cd, Hg, Al, Ga, In, Tl, Si, Ge, Sn, Pb, P, As, Sb, and Bi; or a transition metal selected from the group consisting of Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os, Co, Rh, Ir, Ni, Pd, Pt, Cu, Ag, and Au.

10. The naphthalocyanine dye according to claim 1 wherein the metal M is In (indium).

11. The naphthalocyanine dye according to claim 1 wherein X is $SO_3Z$, with Z being independently selected from the group consisting of H and a monovalent metal cation selected from the group consisting of $Na^+$, $K^+$ and $NR_4^+$, wherein R is independently selected from the group consisting of H, an alkyl group, a substituted alkyl group, an aryl group and a substituted aryl group.

12. The naphthalocyanine dye according to claim 1 wherein X is $SO_3Z$, with Z being Na.

13. An inkjet ink formulation comprising the naphthalocyanine dye defined in claim 1, wherein said naphthalocyanine dye is either soluble or dispersed in the inkjet ink.

14. A detection system, comprising:
a near infrared (NIR) illumination source;
a medium that comprises the naphthalocyanine dye defined in claim 1; and
an NIR sensor that detects absorption of the naphthalocyanine dye in the medium illuminated by the NIR illumination source.

15. The detection system according to claim 14, wherein the medium is an inkjet ink formulation, the naphthalocyanine dye defined in claim 1 being both dispersed in the inkjet ink formulation and stable in the inkjet ink formulation for a shelf life of the inkjet ink formulation, and wherein the NIR illumination source is directed at a nozzle output of an inkjet print head of an inkjet printer, the NIR sensor detecting a presence or an absence of the inkjet ink formulation at the nozzle output with naphthalocyanine dye absorption, the NIR sensor communicating with the inkjet printer.

* * * * *

UNITED STATES PATENT AND TRADEMARK OFFICE
CERTIFICATE OF CORRECTION

PATENT NO.         : 8,795,422 B2  
APPLICATION NO.    : 13/387482  
DATED              : August 5, 2014  
INVENTOR(S)        : Sivapackia Ganapathiappan et al.

Page 1 of 1

It is certified that error appears in the above-identified patent and that said Letters Patent is hereby corrected as shown below:

In the Claims

Column 36, line 24, in Claim 7, delete "range" and insert -- ranges --, therefor.

Column 36, line 30, in Claim 9, delete "TI," and insert -- Ti, --, therefor.

Signed and Sealed this  
Tenth Day of February, 2015

Michelle K. Lee  
*Deputy Director of the United States Patent and Trademark Office*